United States Patent
Cauthen

(10) Patent No.: US 6,997,956 B2
(45) Date of Patent: *Feb. 14, 2006

(54) SPINAL DISC ANNULUS RECONSTRUCTION METHOD AND SPINAL DISC ANNULUS STENT

(75) Inventor: Joseph C. Cauthen, Gainesville, FL (US)

(73) Assignee: Anulex Technologies, Inc., Minnetonka, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/392,729

(22) Filed: Mar. 19, 2003

(65) Prior Publication Data

US 2003/0163200 A1    Aug. 28, 2003

Related U.S. Application Data

(63) Continuation of application No. 09/947,078, filed on Sep. 5, 2001, now Pat. No. 6,592,625, which is a continuation of application No. 09/484,706, filed on Jan. 18, 2000, now abandoned.

(60) Provisional application No. 60/160,710, filed on Oct. 20, 1999.

(51) Int. Cl.
*A61F 2/44* (2006.01)

(52) U.S. Cl. .................. 623/17.16; 623/902; 128/898; 600/37; 606/151

(58) Field of Classification Search ............... 623/902, 623/11.11, 17.11, 17.12, 17.16; 606/60–61, 606/151, 153–156, 191, 192, 108, 213, 215, 606/216, 219, 220; 128/898; 600/37
See application file for complete search history.

(56) References Cited

U.S. PATENT DOCUMENTS

| | | | |
|---|---|---|---|
| 3,867,728 A | 2/1975 | Stubstead et al. | |
| 4,013,078 A | 3/1977 | Felid | |
| 4,059,115 A | 11/1977 | Jumashev et al. | |
| 4,545,374 A | 10/1985 | Jacobson | |
| 4,741,330 A | 5/1988 | Hayhurst | |
| 4,772,287 A | 9/1988 | Ray et al. | |

(Continued)

FOREIGN PATENT DOCUMENTS

DE      4323595 C1    7/1994

(Continued)

OTHER PUBLICATIONS

Ahlgren, B. D., M.D., et al., Annular Incision Technique on the Strength and Multidirectional Flexibility of the Healing Intervertebral Disc, SPINE vol. 19, No. 8, pp 948-954; J. B. Lippincott Company, 1994.

(Continued)

*Primary Examiner*—David J. Isabella
*Assistant Examiner*—Urmi Chattopadhyay
(74) *Attorney, Agent, or Firm*—Saliwanchik, Lloyd & Saliwanchik

(57) ABSTRACT

A surgical method of repair and reconstruction of the spinal disc wall (annulus) after surgical invasion or pathologic rupture, incorporating suture closure, or stent insertion and fixation, designed to reduce the failure rate of conventional surgical procedures on the spinal discs. The design of the spinal disc annulus stent allows ingrowth of normal cells of healing in an enhanced fashion strengthening the normal reparative process.

29 Claims, 7 Drawing Sheets

U.S. PATENT DOCUMENTS

| | | |
|---|---|---|
| 4,852,568 A | 8/1989 | Kensey |
| 4,873,976 A | 10/1989 | Schreiber |
| 4,890,612 A | 1/1990 | Kensey |
| 4,904,260 A | 2/1990 | Ray et al. |
| 4,932,969 A | 6/1990 | Frey et al. |
| 5,015,255 A | 5/1991 | Kuslich |
| 5,021,059 A | 6/1991 | Kensey et al. |
| 5,061,274 A | 10/1991 | Kensey |
| 5,108,438 A | 4/1992 | Stone |
| 5,122,154 A | 6/1992 | Rhodes |
| 5,171,278 A | 12/1992 | Pisharodi et al. |
| 5,195,541 A | 3/1993 | Obenchain |
| 5,204,106 A | 4/1993 | Schepers et al. |
| 5,258,000 A | 11/1993 | Gianturco |
| 5,258,043 A | 11/1993 | Stone |
| 5,269,783 A | 12/1993 | Sander |
| 5,313,962 A | 5/1994 | Obenchain |
| 5,320,633 A | 6/1994 | Allen et al. |
| 5,336,460 A | 8/1994 | Hettinga |
| 5,342,393 A | 8/1994 | Stack |
| 5,356,432 A | 10/1994 | Rutkow et al. |
| 5,366,460 A | 11/1994 | Eberbach |
| 5,368,602 A | 11/1994 | De la Torre |
| 5,376,120 A | 12/1994 | Sarver et al. |
| 5,390,683 A | 2/1995 | Pisharodi |
| 5,397,331 A | 3/1995 | Himpens et al. |
| 5,397,991 A | 3/1995 | Rogers |
| 5,439,464 A | 8/1995 | Shapiro |
| 5,500,000 A | 3/1996 | Feagin et al. |
| 5,507,754 A | 4/1996 | Green et al. |
| 5,531,759 A | 7/1996 | Kensey et al. |
| 5,534,028 A | 7/1996 | Bao et al. |
| 5,545,178 A | 8/1996 | Kensey et al. |
| 5,549,617 A | 8/1996 | Green et al. |
| 5,549,679 A | 8/1996 | Kuslich |
| 5,556,429 A | 9/1996 | Felt |
| 5,562,689 A | 10/1996 | Green et al. |
| 5,562,736 A | 10/1996 | Ray et al. |
| 5,569,242 A | 10/1996 | Lax et al. |
| 5,571,189 A | 11/1996 | Kuslich |
| 5,599,279 A | 2/1997 | Slotman et al. |
| 5,634,944 A | 6/1997 | Magram |
| 5,645,597 A | 7/1997 | Krapiva |
| 5,649,945 A | 7/1997 | Ray et al. |
| 5,662,681 A | 9/1997 | Nash et al. |
| 5,681,310 A | 10/1997 | Yuan et al. |
| 5,702,454 A | 12/1997 | Baumgartner |
| 5,716,416 A | 2/1998 | Lin |
| 5,733,337 A | 3/1998 | Carr et al. |
| 5,755,797 A | 5/1998 | Baumgartner |
| 5,766,246 A | 6/1998 | Mulhauser et al. |
| 5,782,844 A | 7/1998 | Yoon et al. |
| 5,782,860 A | 7/1998 | Epstein et al. |
| 5,785,705 A | 7/1998 | Baker |
| 5,788,625 A | 8/1998 | Plouhar et al. |
| 5,800,549 A | 9/1998 | Bao et al. |
| 5,824,093 A | 10/1998 | Ray et al. |
| 5,827,298 A | 10/1998 | Hart et al. |
| 5,849,331 A | 12/1998 | Ducheyne et al. |
| 5,879,366 A | 3/1999 | Shaw et al. |
| 5,888,220 A | 3/1999 | Felt et al. |
| 5,904,703 A | 5/1999 | Gilson |
| 5,916,225 A | 6/1999 | Kugel |
| 5,922,028 A | 7/1999 | Plouhar et al. |
| 5,928,284 A | 7/1999 | Mehdizadeh |
| 5,935,147 A | 8/1999 | Kensey et al. |
| 5,954,767 A | 9/1999 | Pajotin et al. |
| 5,964,807 A | 10/1999 | Gan et al. |
| 5,972,022 A | 10/1999 | Huxel |
| 5,976,174 A | 11/1999 | Ruiz |
| 5,976,186 A | 11/1999 | Bao et al. |
| 5,980,504 A | 11/1999 | Sharkey et al. |
| 6,007,570 A | 12/1999 | Sharkey et al. |
| 6,019,792 A | 2/2000 | Cauthen |
| 6,053,909 A | 4/2000 | Shadduck |
| 6,066,776 A | 5/2000 | Goodwin et al. |
| 6,073,051 A | 6/2000 | Sharkey et al. |
| 6,095,149 A | 8/2000 | Sharkey et al. |
| 6,099,514 A | 8/2000 | Sharkey et al. |
| 6,126,682 A | 10/2000 | Sharkey et al. |
| 6,140,452 A | 10/2000 | Felt et al. |
| 6,171,318 B1 | 1/2001 | Kugel et al. |
| 6,179,874 B1 | 1/2001 | Cauthen |
| 6,183,518 B1 | 2/2001 | Ross et al. |
| 6,187,048 B1 | 2/2001 | Milner et al. |
| 6,206,921 B1 | 3/2001 | Guagliano et al. |
| 6,224,630 B1 | 5/2001 | Bao et al. |
| 6,245,107 B1 | 6/2001 | Ferree |
| 6,248,106 B1 | 6/2001 | Ferree |
| 6,280,453 B1 | 8/2001 | Kugel et al. |
| 6,340,369 B1 | 1/2002 | Ferree |
| 6,344,058 B1 | 2/2002 | Ferree |
| 6,352,557 B1 | 3/2002 | Ferree |
| 6,371,990 B1 | 4/2002 | Ferree |
| 6,425,919 B1 | 7/2002 | Lambrecht |
| 6,425,924 B1 | 7/2002 | Rousseau |
| 6,428,576 B1 * | 8/2002 | Haldimann ............... 623/17.16 |
| 6,447,531 B1 | 9/2002 | Amplatz |
| 6,452,924 B1 | 9/2002 | Golden et al. |
| 6,508,828 B1 | 1/2003 | Akerfeldt et al. |
| 6,530,933 B1 | 3/2003 | Yeung et al. |
| 6,592,625 B1 * | 7/2003 | Cauthen ................... 623/17.16 |
| 2001/0004710 A1 * | 6/2001 | Felt et al. ................. 623/17.12 |
| 2002/0189622 A1 * | 12/2002 | Cauthen et al. ............. 128/898 |

FOREIGN PATENT DOCUMENTS

| | | |
|---|---|---|
| GB | 2054383 | 2/1981 |
| WO | WO 91/16867 A1 | 11/1991 |
| WO | WO 94/23671 A1 | 10/1994 |
| WO | WO 95/22285 A1 | 8/1995 |
| WO | WO 95/31946 A1 | 11/1995 |
| WO | WO 95/31948 A1 | 11/1995 |
| WO | WO 9531946 A1 * | 11/1995 |
| WO | WO 96/27339 A1 | 9/1996 |
| WO | WO 97/20874 A1 | 6/1997 |
| WO | WO 97/26847 A1 | 7/1997 |
| WO | WO 98/01091 A1 | 1/1998 |
| WO | WO 98/22050 A1 | 5/1998 |
| WO | WO 99/00074 A1 | 1/1999 |
| WO | WO 99/02108 A1 | 1/1999 |
| WO | WO 99/04720 A1 | 2/1999 |
| WO | WO 99/16381 A1 | 4/1999 |
| WO | WO 98/05274 A1 | 10/1999 |
| WO | WO 99/61084 A1 | 12/1999 |
| WO | WO 00/20021 A1 | 4/2000 |
| WO | WO 00/25706 A1 | 5/2000 |
| WO | WO 00/42953 A1 | 7/2000 |
| WO | WO 00/49978 A1 | 8/2000 |
| WO | WO 00/61037 A1 | 10/2000 |
| WO | WO 00/62832 A1 | 10/2000 |
| WO | WO 00/76409 A1 | 12/2000 |
| WO | WO 01/10316 A1 | 2/2001 |
| WO | WO 01/12107 A1 | 2/2001 |
| WO | WO 01/21246 A1 | 3/2001 |
| WO | WO 01/22902 A2 | 4/2001 |
| WO | WO 01/26570 A1 | 4/2001 |
| WO | WO 01/28464 A1 | 4/2001 |
| WO | WO 01/45577 A2 | 6/2001 |
| WO | WO 01/93784 A2 | 12/2001 |
| WO | WO 01/95818 A1 | 12/2001 |
| WO | WO 02/17825 A3 | 3/2002 |

OTHER PUBLICATIONS

Ahlgren, Bradley D., et al., Effect of Annular Repair on the Healing Strength of the Intervertebral Disc, SPINE vol. 25, No. 17, pp 2165-2170, Lippincott Williams & Wilkins, Inc., 2000.

Cauthen, Joseph C., M.D., "Microsurgical Annular Reconstruction (Annuloplasty) Following Lumbar Microdiscectomy: Preliminary Report of a New Technique", Abstract for Poster Presentation, AANS/CNS Section On Disorders Of The Spine And Peripheral Nerves Annual Meeting, 1999.

Lehmann, Thomas R., M.D., et al., Refinements In Technique For Open Lumbar Discectomy, International Society for the Study of the Lumbar Spine, Jun. 2-6, 1997.

Ordway, N. R., et al., "Failure Properties Of A Hydrogel Nucleus In The Intervertebral Disc", North American Spine Society, Oct. 2-25, 1997.

Osti, O. L., et al., "Annular Tears And Disc Degeneration In The Lumber Spine", The Journal of Bone and Joint Surgery, vol. 74-B, No. 5, pp 678-682; Sep. 1992.

Panjabi, Manohar, Ph.D., et al., "Intrinsic Disc Pressure as a Measure Of Integrity of the Lumbar Spine", SPINE vol. 13, No. 8, pp 913-917; 1988.

Ray, Charles D., Prosthetic Disc Nucleus Implants: Update, North American Spine Society 13th Annual Meeting, pp 252.

Yasargil, M. G., "Microsurgical Operation of Herniated Lumbar Disc", pp 81, in Lumbar Disc Adult Hydrocephalus edited by R. Wullenweber et al., Springer-Verlag, Berlin Heidelberg New York 1977.

Cauthen, Joseph, Draft Abstract entitled "Microsurgical Annular Reconstruction (Annulogplasty) Following Lumbar Microdiscectomy: Preliminary Report of a New Technique" from abstracts@neurosurgery.org, Sep. 4, 1998.

Cauthen, Joseph C., "Annulotomy Study Preliminary Results: Updated Feb. 1999 for all procedures with at least one-year follow up" (Table), Feb. 8, 1999.

* cited by examiner

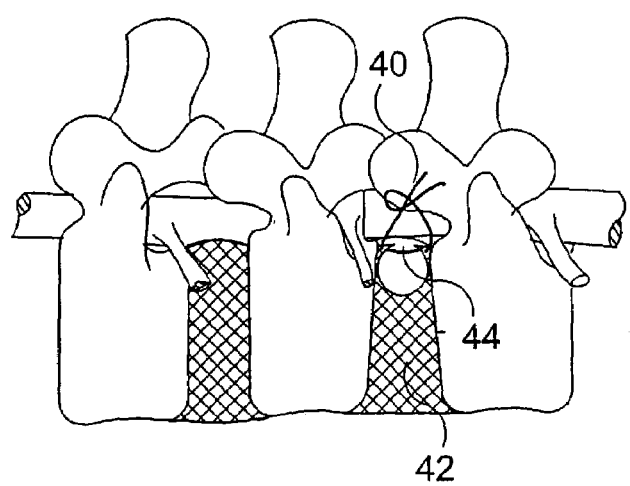
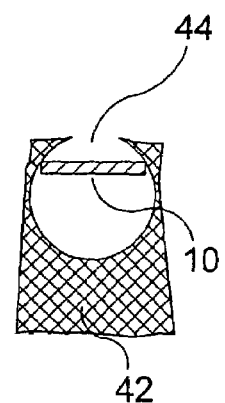
FIG. 7A
FIG. 7B
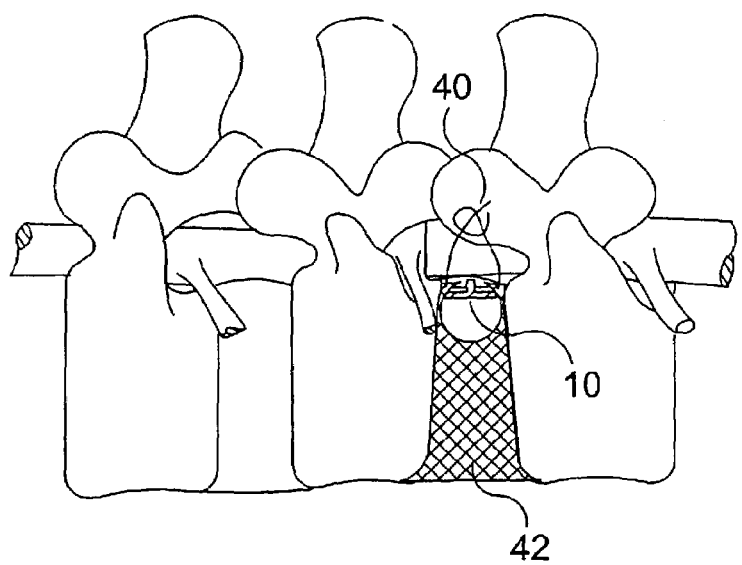
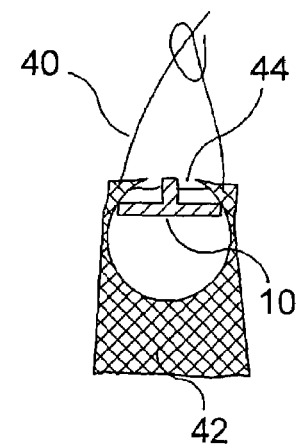
FIG. 8A
FIG. 8B

SPINAL DISC ANNULUS RECONSTRUCTION METHOD AND SPINAL DISC ANNULUS STENT

CROSS-REFERENCE TO A RELATED APPLICATION

This application is a continuation of U.S. Ser. No. 09/947,078, filed Sep. 5, 2001 now U.S. Pat. No. 6,592,625; which is a continuation of U.S. Ser. No. 09/484,706, filed Jan. 18,2000 (now abandoned); which claims the benefit of U.S. Provisional Application No. 60/160,710, filed Oct. 20, 1999.

FIELD OF THE INVENTION

The invention generally relates to a surgical method of intervertebral disc wall reconstruction. The invention also relates to an annular repair device, or stent, for annular disc repair. The effects of said reconstruction are restoration of disc wall integrity and reduction of the failure rate (3–21%) of a common surgical procedure (disc fragment removal or discectomy). This surgical procedure is performed about 390,000 times annually in the United States.

BACKGROUND OF THE INVENTION

The spinal column is formed from a number of vertebrae, which in their normal state are separated from each other by cartilaginous intervertebral discs. The intervertebral disc acts in the spine as a crucial stabilizer, and as a mechanism for force distribution between the vertebral bodies. Without the disc, collapse of the intervertebral space occurs in conjunction with abnormal joint mechanics and premature development of arthritic changes.

The normal intervertebral disc has an outer ligamentous ring called the annulus surrounding the nucleus pulposus. The annulus binds the adjacent vertebrae together and is constituted of collagen fibers that are attached to the vertebrae and cross each other so that half of the individual fibers will tighten as the vertebrae are rotated in either direction, thus resisting twisting or torsional motion. The nucleus pulposus is constituted of loose tissue, having about 85% water content, which moves about during bending from front to back and from side to side.

The aging process contributes to gradual changes in the intervertebral discs. The annulus loses much of its flexibility and resilience, becoming more dense and solid in composition. The aging annulus is also marked by the appearance on propagation of cracks or fissures in the annular wall. Similarly, the nucleus dessicates, increasing viscosity and thus losing its fluidity. In combination, these features of the aged intervertebral discs result in less dynamic stress distribution because of the more viscous nucleus pulposus, and less ability to withstand localized stresses by the annulus fibrosus due to its dessication, loss of flexibility and the presence of fissures. Occasionally fissures may form rents through the annular wall. In these instances, the nucleus pulposus is urged outwardly from the subannular space through a rent, often into the spinal column. Extruded nucleus pulposus can, and often does, mechanically press on the spinal cord or spinal nerve rootlet. This painful condition is clinically referred to as a ruptured or herniated disc.

In the event of annulus rupture, the subannular nucleus pulposus migrates along the path of least resistance forcing the fissure to open further, allowing migration of the nucleus pulposus through the wall of the disc, with resultant nerve compression and leakage of chemicals of inflammation into the space around the adjacent nerve roots supplying the extremities, bladder, bowel and genitalia. The usual effect of nerve compression and inflammation is intolerable back or neck pain, radiating into the extremities, with accompanying numbness, weakness, and in late stages, paralysis and muscle atrophy, and/or bladder and bowel incontinence. Additionally, injury, disease or other degenerative disorders may cause one or more of the intervertebral discs to shrink, collapse, deteriorate or become displaced, herniated, or otherwise damaged and compromised.

The surgical standard of care for treatment of herniated, displaced or ruptured intervertebral discs is fragment removal and nerve decompression without a requirement to reconstruct the annular wall. While results are currently acceptable, they are not optimal. Various authors report 3.1–21% recurrent disc herniation, representing a failure of the primary procedure and requiring re-operation for the same condition. An estimated 10% recurrence rate results in 39,000 re-operations in the United States each year.

An additional method of relieving the symptoms is thermal annuloplasty, involving the heating of sub-annular zones in the non-herniated painful disc, seeking pain relief, but making no claim of reconstruction of the ruptured, discontinuous annulus wall.

There is currently no known method of annulus reconstruction, either primarily or augmented with an annulus stent.

BRIEF SUMMARY OF THE INVENTION

The present invention provides methods and related materials for reconstruction of the disk wall in cases of displaced, herniated, ruptured, or otherwise damaged intervertebral discs. In accordance with the invention, an annulus stent is disclosed for repair of an intervertebral disc annulus, comprising a centralized hub section, said hub section comprising lateral extensions from the hub section.

In an exemplary embodiment, one or more mild biodegradable surgical sutures are placed at about equal distances along the sides of a pathologic aperture in the ruptured disc wall (annulus) or along the sides of a surgical incision in the annular wall, which may be weakened or thinned.

In another embodiment as depicted in FIG. 7B, the method can be augmented by creating a subannular barrier in and across the aperture by placement of a patch of human muscle fascia (the membrane covering the muscle) or any other autograft, autograft, or xenograft acting as a bridge or a scaffold, providing a platform for traverse of fibroblasts or other normal cells of repair existing in and around the various layers of the disc annulus, prior to closure of the aperture.

A 30–50% reduction in the rate of recurrence of disc herniation has been achieved using the aforementioned fascial augmentation with this embodiment.

Having demonstrated that human muscle fascia is adaptable for annular reconstruction, other biocompatible membranes can be employed as a bridge, stent, patch or barrier to subsequent migration of the disc nucleus through the aperture. Such biocompatible materials may be, for example, medical grade biocompatible fabrics, biodegradable polymeric sheets, or form fitting or non-form fitting fillers for the cavity created by removal of a portion of the disc nucleus pulposus in the course of the disc fragment removal or discectomy. The prosthetic material can be placed in and around the intervertebral space, created by removal of the degenerated disc fragments.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate illustrative embodiments of the invention and, together with the description, serve to explain the principles of the invention.

FIG. 7A–7B shows a primary closure of an opening in the disc annulus.

FIGS. 8A–8B show a primary closure with a stent.

DETAILED DESCRIPTION OF THE INVENTION

Reference will now be made in detail to an illustrative embodiment of the invention, which appears in the accompanying drawings. Wherever possible, the same reference numbers will be used throughout the drawings to refer to the same or like parts.

In one embodiment of the present invention, as shown in FIG. 7A, a damaged annulus 42 is repaired by use of surgical sutures 40. One or more surgical sutures 40 are placed at about equal distances along the sides of a pathologic aperture 44 in the annulus 42. Reapproximation or closure of the aperture 44 is accomplished by tying the sutures 40 so that the sides of the aperture 44 are drawn together. The reapproximation or closure of the aperture 44 enhances the natural healing and subsequent reconstruction by the natural tissue (e.g., fibroblasts) crossing the now surgically narrowed gap in the annulus 42. Preferably, the surgical sutures 40 are biodegradable, but permanent non-biodegradable may be utilized.

Additionally, to repair a weakened or thinned wall of a disc annulus 42, a surgical incision is made along the weakened or thinned region of the annulus 42 and one or more surgical sutures 40 can be placed at about equal distances laterally from the incision. Reapproximation or closure of the incision is accomplished by tying the sutures 40 so that the sides of the incision are drawn together. The reapproximation or closure of the incision enhances the natural healing and subsequent reconstruction by the natural tissue crossing the now surgically narrowed gap in the annulus 42. Preferably, the surgical sutures 40 are biodegradable, but permanent non-biodegradable materials may be utilized.

In an alternative embodiment as depicted in FIG. 7B, the method can be augmented by the placement of a patch of human muscle fascia or any other autograft, autograft or xenograft in and across the aperture 44. The patch acts as a bridge in and across the aperture 44, providing a platform for traverse of fibroblasts or other normal cells of repair existing in and around the various layers of the disc annulus 42, prior to closure of the aperture 44.

In a further embodiment, as shown in FIGS. 8A–B a biocompatible membrane can be employed as an annulus stent 10, being placed in and across the aperture 44. The annulus stent 10 acts as a bridge in and across the aperture 44, providing a platform for a traverse of fibroblasts or other normal cells of repair existing in and around the various layers of the disc annulus 42, prior to closure of the aperture 44.

Figure 1:
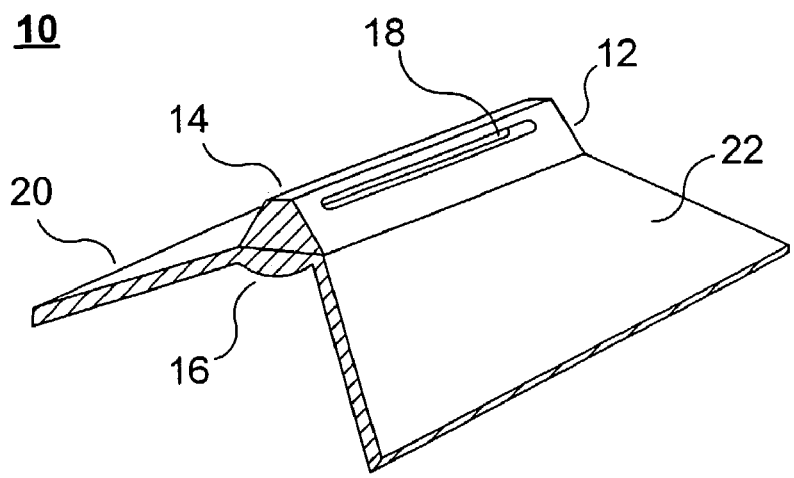
FIG. 1 shows a perspective view of an illustrative embodiment of an annulus stent.
Figure 2:
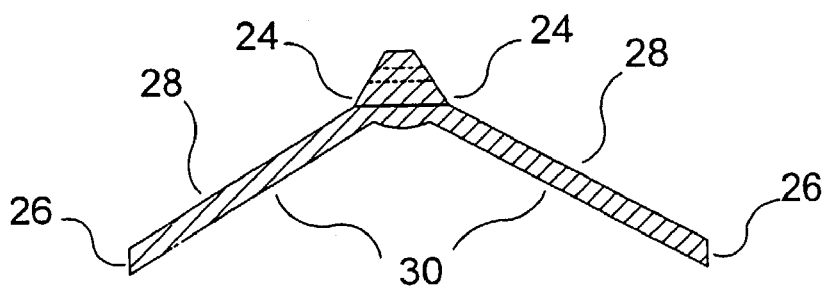
FIG. 2 shows a front view of the annulus stent of FIG. 1.
Figure 3:
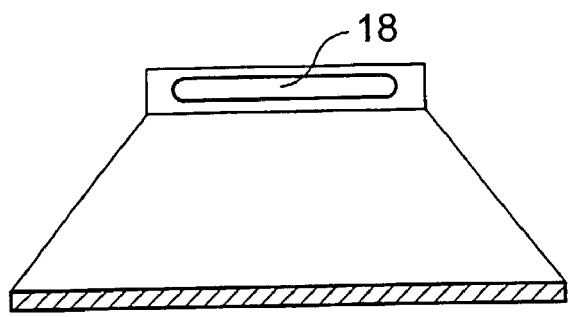
FIG. 3 shows a side view of the annulus stent of FIG. 1.

In an illustrative embodiment, as shown in FIGS. 1–3, the annulus stent 10 comprises a centralized vertical extension 12, with an upper section 14 and a lower section 16. The centralized vertical extension 12 can be trapezoid in shape through the width and may be from about 8 mm–12 mm in length.

Figure 4A:
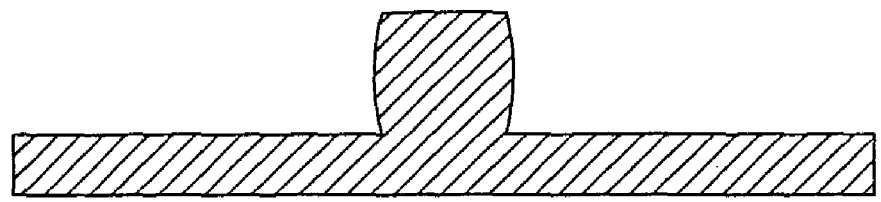
FIGS. 4A–4C show a front view of alternative illustrative embodiments of an annulus stent.
Figure 4B:
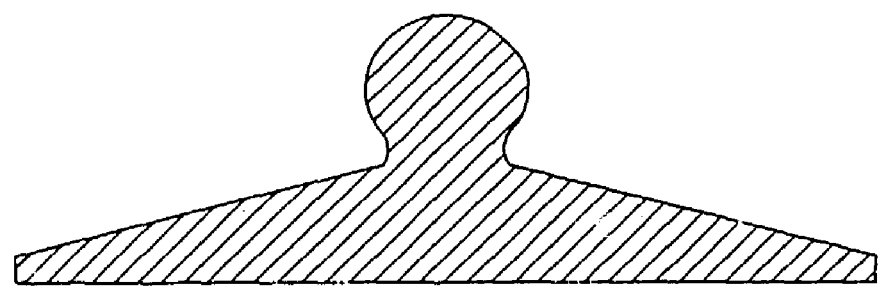
Figure 4C:
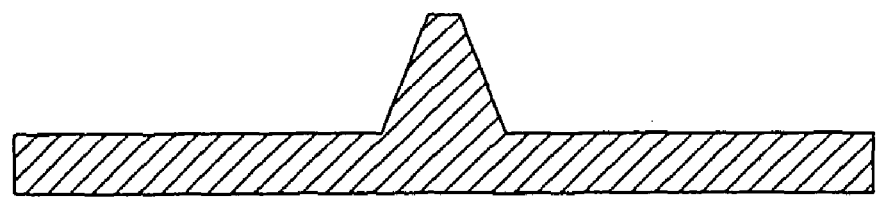

Additionally, the upper section 14 of the centralized vertical extension 12 may be any number of different shapes, as shown in FIGS. 4A and 4B, with the sides of the upper section 14 being curved or with the upper section 14 being circular in shape. Furthermore, the annulus stent 10 may contain a recess between the upper section 14 and the lower section 16, enabling the annulus stent 10 to form a compatible fit with the edges of the aperture 44.

The upper section 14 of the centralized vertical extension 12 can comprise a slot 18, where the slot 18 forms an orifice through the upper section 14. The slot 18 is positioned within the upper section 14 such that it traverses the upper section's 14 longitudinal axis. The slot 18 is of such a size and shape that sutures, tension bands, staples or any other type of fixation device known in the art may be passed through, to affix the annulus stent 10 to the disc annulus 42.

In an alternative embodiment, the upper section 14 of the centralized vertical extension 12 may be perforated. The perforated upper section 14 contains a plurality of holes that traverse the longitudinal axis of upper section 14. The perforations are of such a size and shape that sutures, tension bands, staples or any other type of fixation device known the art may be passed through, to affix the annulus stent 10 to the disc annulus 42.

The lower section 16 of the centralized vertical extension 12 can comprise a pair of lateral extensions, a left lateral extension 20 and a right lateral extension 22. The lateral extensions 20 and 22 comprise an inside edge 24, an outside edge 26, an upper surface 28, and a lower surface 30. The lateral extensions 20 and 22 can have an essentially constant thickness throughout. The inside edge 24 is attached to and is about the same length as the lower section 16. The outside edge 26 can be about 8 mm–16 mm in length. The inside edge 24 and the lower section 16 meet to form a horizontal plane, essentially perpendicular to the centralized vertical extension 12. The upper surface 28 of the lateral extensions 20 and 22 can form an angle from about 0°–60° below the horizontal plane. The width of the annulus stent 10 may be from about 3 mm–5 mm.

Additionally, the upper surface 28 of the lateral extensions 20 and 22 may be barbed for fixation to the inside surface of the disc annulus 42 and to resist expulsion through the aperture 44.

In an alternative embodiment, as shown in FIG. 4B, the lateral extensions 20 and 22 have a greater thickness at the inside edge 24 than at the outside edge 26.

In an illustrative embodiment, the annulus stent 10 is a solid unit, formed from one or more of the flexible resilient biocompatible or bioresorbable materials well know in the art.

For example, the annulus stent 10 may be made from:
a porous matrix or mesh of biocompatible and bioresorbable fibers acting as a scaffold to regenerate disc tissue and replace annulus fibrosus as disclosed in, for example, U.S. Pat. No. 5,108,438 (Stone) and U.S. Pat. No. 5,258,043 (Stone), a strong network of inert fibers intermingled with a bioresorbable (or bioabsorable) material which attracts tissue ingrowth as disclosed in, for example, U.S. Pat. No. 4,904,260 (Ray et al.);
a biodegradable substrate as disclosed in, for example, U.S. Pat. No. 5,964,807 (Gan at al.); or
an expandable polytetrafluoroethylene (ePTFE), as used for conventional vascular grafts, such as those sold by W.L. Gore and Associates, Inc. under the trademarks GORE-TEX and PRECLUDE, or by Impra, Inc. under the trademark IMPRA.

Furthermore, the annulus stent 10, may contain hygroscopic material for a controlled limited expansion of the annulus stent 10 to fill the evacuated disc space cavity.

Additionally, the annulus stent 10 may comprise materials to facilitate regeneration of disc tissue, such as bioactive silica-based materials that assist in regeneration of disc tissue as disclosed in U.S. Pat. No. 5,849,331 (Ducheyne, et al.), or other tissue growth factors well known in the art.

Figure 5A:
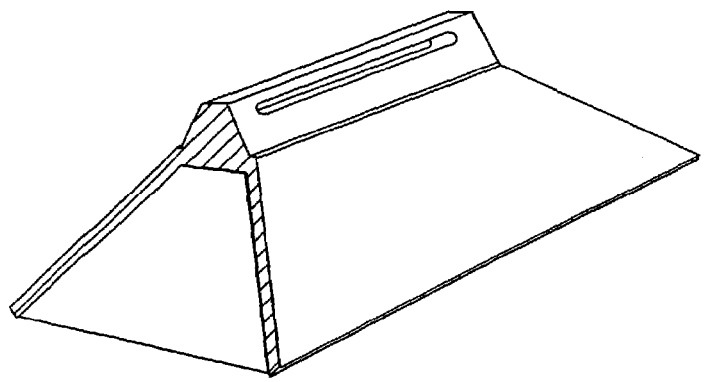
FIGS. 5A–5B show the alternative embodiment of a further illustrative embodiment of an annulus stent.
Figure 5B:
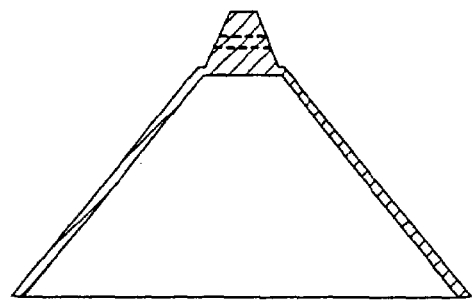
Figure 6A:
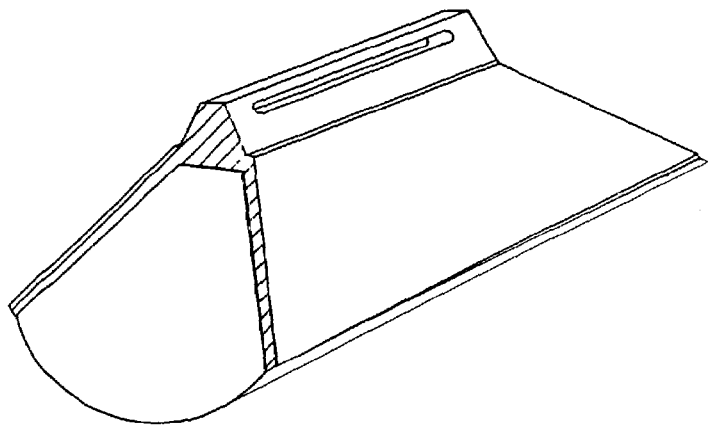
FIGS. 6A–6B show the alternative embodiment of a further illustrative embodiment of an annulus stent.
Figure 6B:
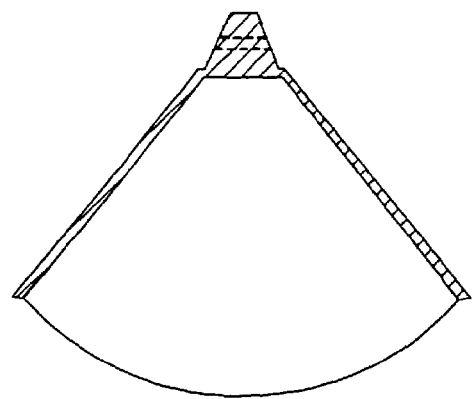

In further embodiments, as shown in FIGS. 5AB–6AB, the left and right lateral extensions 20 and 22 join to form a solid pyramid or cone. Additionally, the left and right lateral extensions 20 and 22 may form a solid trapezoid, wedge, or bullet shape. The solid formation may be a solid biocompatible or bioresorbable flexible material, allowing the lateral extensions 20 and 22 to be compressed for insertion into aperture 44, then to expand conforming to the shape of the annulus ' 42 inner wall.

Alternatively, a compressible core may be attached to the lower surface 30 of the lateral extensions 20 and 22, forming a pyramid, cone, trapezoid, wedge, or bullet shape. The compressible core may be made from one of the biocompatible or bioresorbable resilient foams well known in the art. The core can also comprise a fluid-expandable membrane, e.g., a balloon. The compressible core allows the lateral extensions 20 and 22 to be compressed for insertion into aperture 44, then to expand conforming to the shape of the annulus ' 42 inner wall and to the cavity created by pathologic extrusion or surgical removal of the disc fragment.

In an illustrative method of use, as shown in FIGS. 11A–D, the lateral extensions 20 and 22 are compressed together for insertion into the aperture 44 of the disc annulus 42. The annulus stent 10 is then inserted into the aperture 44, where the lateral extensions 20, 22 expand. In an expanded configuration, the upper surface 28 can substantially conform to the contour of the inside surface of the disc annulus 42. The upper section 14 is positioned within the aperture 44 so that the annulus stent 10 may be secured to the disc annulus 42, using means well known in the art.

In an alternative method, where the length of the aperture 44 is less than the length of the outside edge 26 of the annulus stent 10, the annulus stent 10 can be inserted laterally into the aperture 44. The lateral extensions 20 and 22 are compressed, and the annulus stent 10 can then be laterally inserted into the aperture 44. The annulus stent 10 can then be rotated inside the disc annulus 42, such that the upper section 14 can be held back through the aperture 44. The lateral extensions 20 and 22 are then allowed to expand, with the upper surface 28 contouring to the inside surface of the disc annulus 42. The upper section 14 can be positioned within, or proximate to, the aperture 44 in the subannular space such that the annulus stent 10 may be secured to the disc annulus, using means well known in the art.

Figure 9:
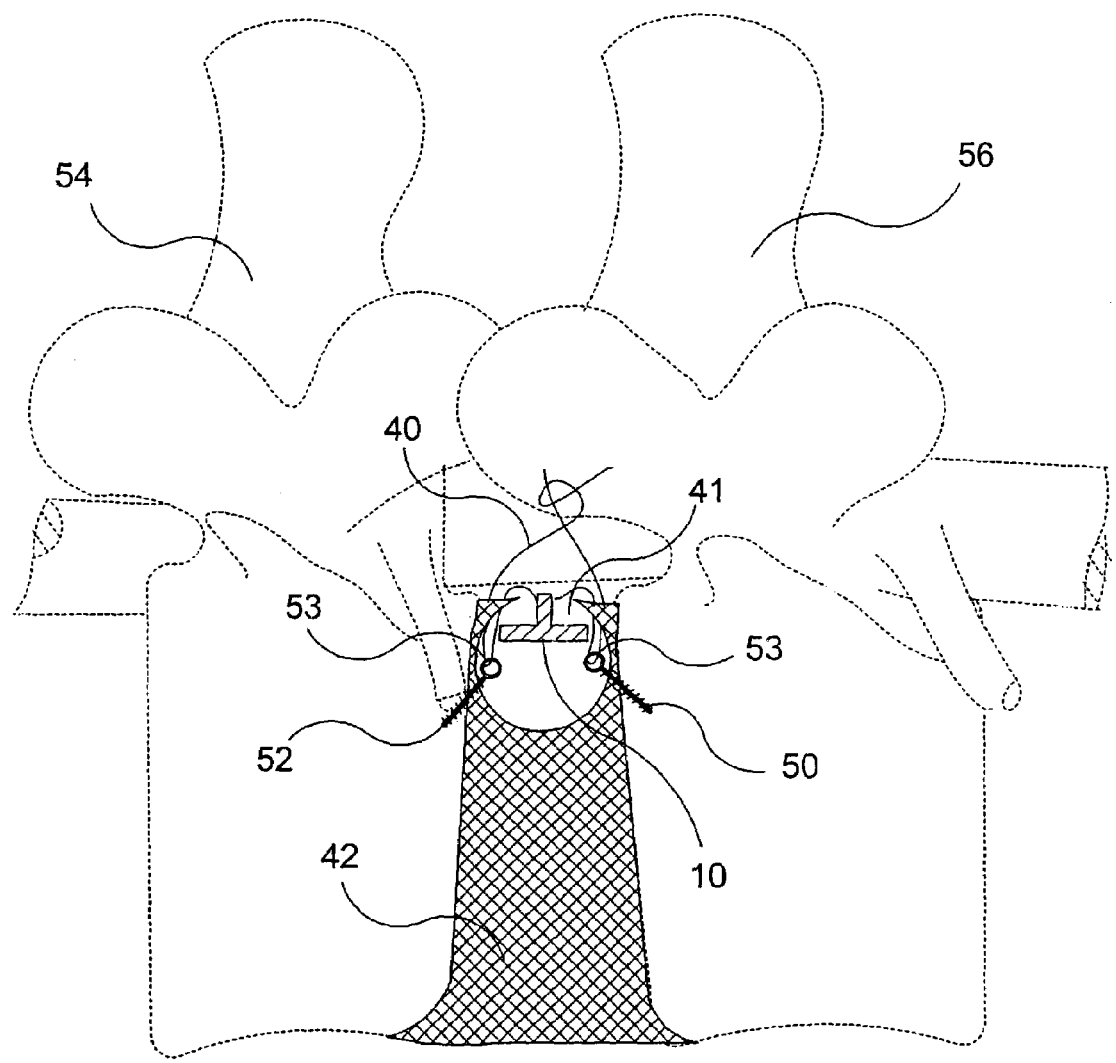
FIG. 9 shows a method of suturing an annulus stent into the disc annulus, utilizing sub-annular fixation points.

In an alternative method of securing the annulus stent 10 in the aperture 44, as shown in FIG. 9, a first surgical screw 50 and second surgical screw 52, with eyeholes 53 located at the top of the screws 50 and 52, are opposingly inserted into the adjacent vertebrae 54 and 56 below the annulus stent 10. After insertion of the annulus stent 10 into the aperture 44, a suture 40 is passed down though the disc annulus 42, adjacent to the aperture 44, through the eye hole 53 on the first screw 50 then back up through the disc annulus 42 and through the orifice 18 on the annulus stent 10. This is repeated for the second screw 52, after which the suture 40 is secured. One or more surgical sutures 40 are placed at about equal distances along the sides of the aperture 44 in the disc annulus 42. Reapproximation or closure of the aperture 44 is accomplished by tying the sutures 40 in such a fashion that the sides of the aperture 44 are drawn together. The reapproximation or closure of the aperture 44 enhances the natural healing and subsequent reconstruction by the natural tissue crossing the now surgically narrowed gap in the annulus 42. Preferably, the surgical sutures 40 are biodegradable but permanent non-biodegradable forms may be utilized. This method should decrease the strain on the disc annulus 42 adjacent to the aperture 44, precluding the tearing of the sutures through the disc annulus 42.

It is anticipated that fibroblasts will engage the fibers of the polymer or fabric of the intervertebral disc stent 10, forming a strong wall duplicating the currently existing condition of healing seen in the normal reparative process.

Figure 10A:
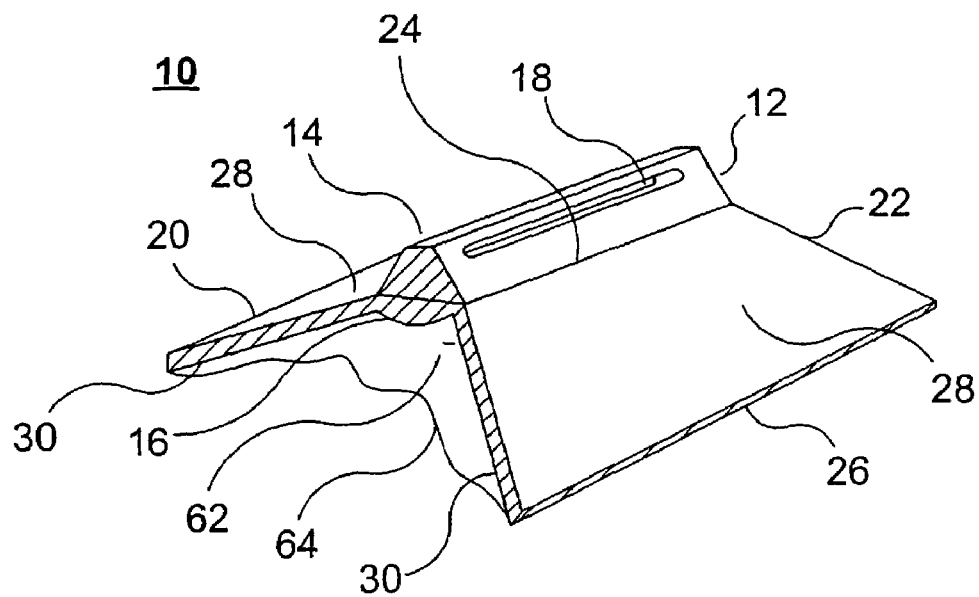
FIGS. 10A–10B show a further illustrative embodiment of an annulus stent with flexible bladder being expanded into the disc annulus.
Figure 10B:
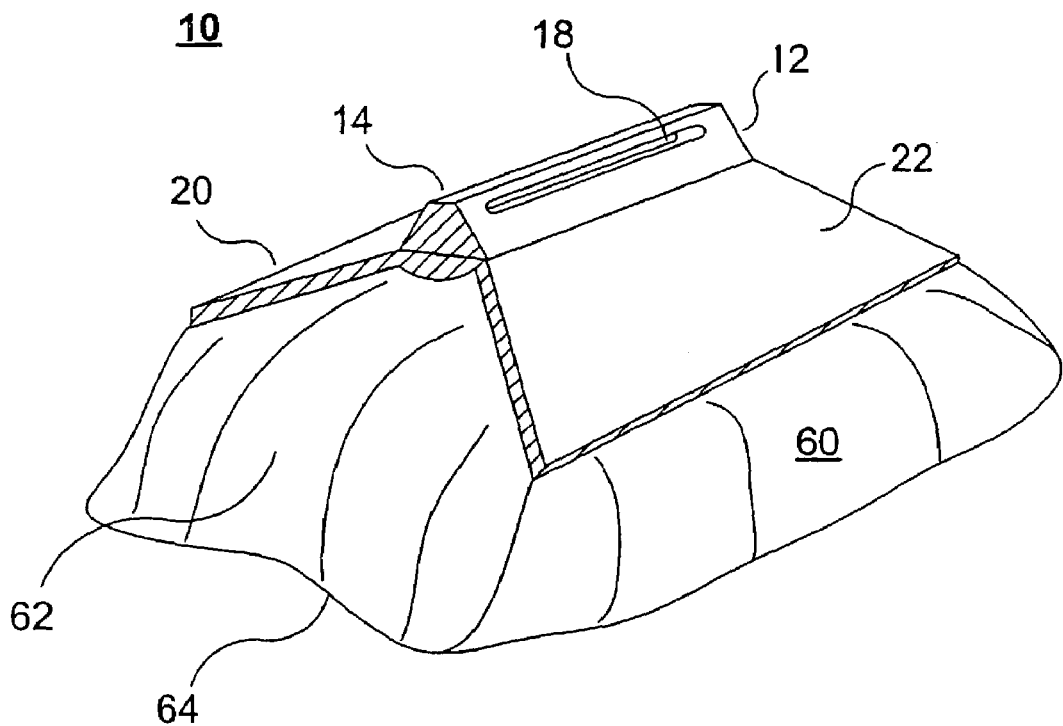
Figure 11A:
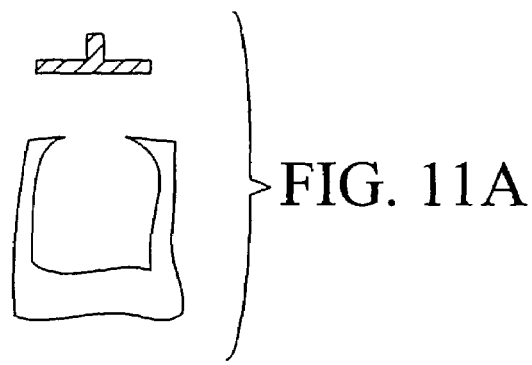
FIGS. 11A–11D show an annulus stent being inserted into the disc annulus.

In an additional embodiment, as shown in FIGS. 10A–B, a flexible bladder 60 is attached to the lower surface 30 of the annulus stent 10. The flexible bladder 60 comprises an internal cavity 62 surrounded by a membrane 64, where the membrane 64 is made from a thin flexible biocompatible material. The flexible bladder 60 is attached to the lower surface 30 of the annulus stent 10 in an unexpanded condition. The flexible bladder 60 is expanded by injecting a biocompatible fluid or expansive foam, as known in the art, into the internal cavity 62. The exact size of the flexible bladder 60 can be varied for different individuals. The typical size of an adult nucleus is about 2 cm in the semi-minor axis, 4 cm in the semi-major axis, and 1.2 cm in thickness.

In an alternative embodiment, the membrane 64 is made of a semi-permeable biocompatible material.

In an illustrative embodiment, a hydrogel is injected into the internal cavity 62 of the flexible bladder 60. A hydrogel is a substance formed when an organic polymer (natural or synthetic) is cross-linked via, covalent, ionic, or hydrogen bonds to create a three-dimensional open-lattice structure, which entraps water molecules to form a gel. The hydrogel may be used in either the hydrated or dehydrated form.

Figure 12A:
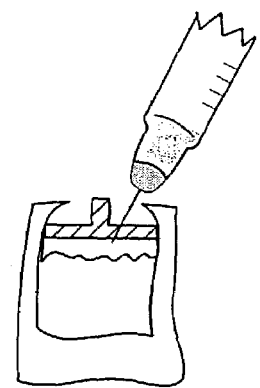
FIGS. 12A–12B show an annulus stent with a flexible bladder being expanded.
Figure 11B:
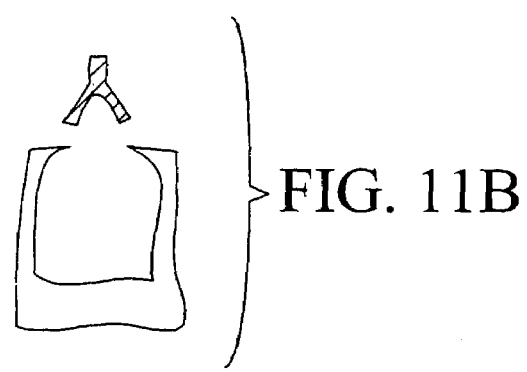
Figure 11C:
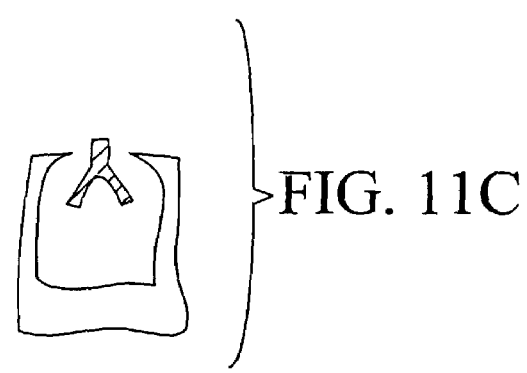
Figure 12B:
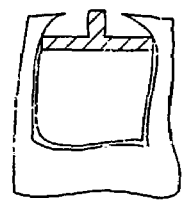
Figure 11D:
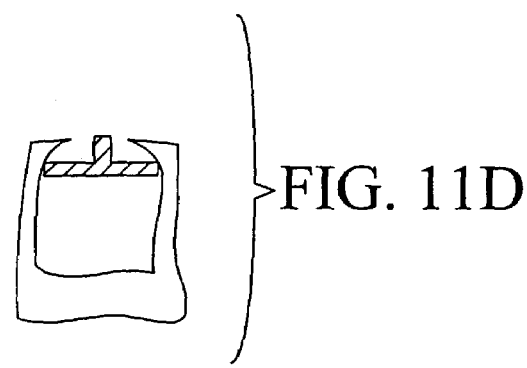

In a method of use, where the annulus stent 10 has been inserted into the aperture 44, as has been previously described and shown in FIGS. 12A–B, an injection instrument, as known in the art, such as a syringe, is used to inject the biocompatible fluid or expansive foam into the internal cavity 62 of the flexible bladder 60. The biocompatible fluid or expansive foam is injected through the annulus stent 10 into the internal cavity 62 of the flexible bladder 60. Sufficient material is injected into the internal cavity 62 to expand the flexible bladder 60 to fill the void in the intervertebral disc cavity. The use of the flexible bladder 60 is particularly useful when it is required to remove all or part of the intervertebral disc nucleus.

The surgical repair of an intervertebral disc may require the removal of the entire disc nucleus, being replaced with an implant, or the removal of a portion of the disc nucleus thereby leaving a void in the intervertebral disc cavity. The flexible bladder 60 allows for the removal of only the damaged section of the disc nucleus, with the expanded flexible bladder 60 filling the resultant void in the intervertebral disc cavity. A major advantage of the annulus stent 10 with the flexible bladder 60 is that the incision area in the annulus 42 can be reduced in size, as there is no need for the insertion of an implant into the intervertebral disc cavity.

In an alternative method of use, a dehydrated hydrogel is injected into the internal cavity 62 of the flexible bladder 60. Fluid, from the disc nucleus, passes through the semipermeable membrane 64 hydrating the dehydrated hydrogel. As the hydrogel absorbs the fluid the flexible bladder 60 expands, filling the void in the intervertebral disc cavity.

All patents referred to or cited herein are incorporated by reference in their entirety to the extent they are not inconsistent with the explicit teachings of this specification, including; U.S. Pat. No. 5,108,438 (Stone), U.S. Pat. No. 5,258,043 (Stone), U.S. Pat. No. 4,904,260 (Ray et al.), U.S. Pat. No. 5,964,807 (Gan et al.), U.S. Pat. No. 5,849,331 (Ducheyne et al.), U.S. Pat. No. 5,122,154 (Rhodes), U.S. Pat. No. 5,204,106 (Schepers at al.), U.S. Pat. No. 5,888,220 (Felt et al.) and U.S. Pat. No. 5,376,120 (Sarver et al.).

It should be understood that the examples and embodiments described herein are for illustrative purposes only and that various modifications or changes in light thereof will be suggested to persons skilled in the art and are to be included within the spirit and preview of this application and the scope of the appended claims.

I claim:

1. A method for primarily treating an annulus fibrosus of an intervertebral disc having an aperture in the annulus fibrosus, wherein the aperture provides a pathway for the migration of intradiscal material from the subannular space, the method comprising the steps of:
   providing a scaffold device having a dimension at least as large as an aperture dimension;
   inserting the device through the aperture into the subannular space; and
   causing or allowing the device to orient in the subannular space whereby said dimension at least partially spans said aperture dimension, wherein said device has a portion that is provided primarily for treating said aperture and serves as a scaffold for cells across the aperture to enhance natural healing.

2. The method of claim 1 wherein the device is comprised at least in part of a shape memory material.

3. The method of claim 1, wherein the device is comprised at least in part of biocompatible fabric.

4. The method of claim 1, wherein the device is at least in part bioabsorbable.

5. The method of claim 1 further comprising the step of treating the annulus tissue surrounding the aperture to reduce the relative motion thereof.

6. The method of claim 5, further comprising the step of reapproximating the aperture.

7. The method of claim 6, wherein the device further comprises at least one element for reapproximating the aperture.

8. The method of claim 1, wherein the device further comprises at least one fixation element for attaching the device to the annulus.

9. The method of claim 1, wherein the aperture is pathologic.

10. The method of claim 1, wherein the aperture is formed at least in part by a surgical incision.

11. A method for treating an intervertebral disc having an aperture in the annulus fibrosus, wherein the method of claim 1 is performed following discectomy.

12. The method of claim 1, further comprising the step of applying sutures to acutely stabilize said device.

13. The method of claim 1, wherein said device is comprised at least in part from autograft.

14. The method of claim 13, wherein said autograft is muscle fascia.

15. The method of claim 1, wherein said device is comprised at least in part from allograft.

16. The method of claim 1, wherein said device is comprised at least in part from a biocompatible membrane.

17. The method of claim 16, wherein said biocompatible membrane is a medical grade biocompatible fabric.

18. The method of claim 16, wherein said biocompatible membrane is a medical grade polymeric sheet.

19. The method of claim 1, wherein said scaffold device is applied at least in part in said aperture.

20. The method of claim 19, wherein said scaffold device comprises a filler.

21. The method of claim 20, wherein said filler is at least in part form-fitting.

22. The method of claim 20, wherein said filler is at least in part non-form-fitting.

23. The method of claim 1, further comprising the step of placing sutures at about equal distances along the sides of the aperture.

24. The method of claim 1, wherein said device is comprised at least in part from xenograft.

25. The method of claim 1, further including the step of providing a device comprised at least in part from a material for facilitating regeneration of disc tissues.

26. The method of claim 25, wherein the material for facilitating regeneration includes at least in part a growth factor.

27. The method of claim 25, wherein the material for facilitating regeneration is at least in part bioactive.

28. The method of claim 27, wherein the material for facilitating regeneration is a silica-based material.

29. The method of claim 1, wherein the device serves as a barrier restricting the migration of intradiscal material through the aperture.

* * * * *

UNITED STATES PATENT AND TRADEMARK OFFICE
CERTIFICATE OF CORRECTION

PATENT NO. : 6,997,956 B2  
DATED : February 14, 2006  
INVENTOR(S) : Joseph C. Cauthen Page 1 of 1

It is certified that error appears in the above-identified patent and that said Letters Patent is hereby corrected as shown below:

<u>Column 2,</u>
Lines 43-44, "annular wall, which may be weakened or thinned.
 In another" should read
 -- annular wall, which may be weakened or thinned.
  Sutures are then tied in such fashion as to draw together the sides of the aperture, effecting reapproximation or closure of the opening, to enhance natural healing and subsequent reconstruction by natural tissue (fibroblasts) crossing the now surgically narrowed gap in the disc annulus.
  A 25-30% reduction in the rate of recurrence of disc nucleus herniation through this aperture, has been achieved using this method.
  In another --.
Line 48, "autograft, autograft" should read -- autograft, allograft --.

<u>Column 4,</u>
Line 11, "autograft, autograft" should read -- autograft, allograft --.

Signed and Sealed this

Sixteenth Day of May, 2006

JON W. DUDAS
*Director of the United States Patent and Trademark Office*